United States Patent [19]

Brennan

[11] Patent Number: 4,883,465
[45] Date of Patent: Nov. 28, 1989

[54] NASAL TAMPON AND METHOD FOR USING

[76] Inventor: H. George Brennan, 1137 Granville, Newport Beach, Calif. 92660

[21] Appl. No.: 197,835

[22] Filed: May 24, 1988

[51] Int. Cl.[4] .............................. A61M 25/00
[52] U.S. Cl. .......................... 604/96; 128/325; 128/342; 604/43
[58] Field of Search ........... 128/325, 344, 342, 207.15; 604/43–45, 96–103

[56] References Cited

U.S. PATENT DOCUMENTS

| | | |
|---|---|---|
| 6,796 | 10/1849 | Haile . |
| 923,303 | 6/1909 | Shults . |
| 1,051,850 | 1/1913 | Sandmark . |
| 1,114,268 | 10/1914 | Kells . |
| 1,235,095 | 7/1917 | Beck . |
| 1,766,341 | 6/1930 | Kulik . |
| 2,050,407 | 8/1936 | Wolff ................................ 128/246 |
| 2,179,964 | 11/1939 | Stevens ............................ 128/148 |
| 2,215,126 | 9/1940 | McMillin .......................... 128/148 |
| 2,265,387 | 12/1941 | McMillin .......................... 128/148 |
| 2,481,488 | 9/1949 | Auzin . |
| 2,490,168 | 12/1949 | Strauss ............................. 128/269 |
| 2,493,326 | 1/1950 | Trinder ............................. 128/325 |
| 2,647,515 | 8/1953 | Pollack et al. .................... 128/325 |
| 2,677,375 | 5/1954 | Raiche ............................. 128/349 |
| 2,691,985 | 10/1954 | Newsom ........................... 128/342 |
| 2,847,997 | 8/1958 | Tibone ............................. 128/325 |
| 2,898,913 | 8/1959 | Ritter et al. .................. 128/325 X |
| 3,049,125 | 8/1962 | Kirwkowitsch .................. 128/325 |
| 3,420,237 | 1/1969 | Fortay ............................. 128/325 |
| 3,516,407 | 6/1970 | Ruggero .......................... 128/325 |
| 3,520,300 | 7/1970 | Flower, Jr. ...................... 128/276 |
| 3,547,126 | 12/1970 | Birtwell ........................... 128/349 |
| 3,570,494 | 3/1971 | Gottchalk ........................ 128/325 |
| 3,659,612 | 5/1972 | Shiley et al. ..................... 128/351 |
| 3,731,692 | 5/1973 | Goodyear ..................... 128/207.15 |
| 3,734,100 | 5/1973 | Walker et al. ................... 128/351 |
| 3,753,439 | 8/1973 | Brugarolas et al. ............... 604/43 |
| 3,758,950 | 9/1973 | Krouzian ........................... 32/33 |
| 3,766,924 | 10/1973 | Pidgeon .......................... 128/349 |
| 3,850,176 | 11/1974 | Gottschalk ....................... 128/325 |
| 3,884,241 | 5/1975 | Walker ............................ 128/325 |
| 3,884,242 | 5/1975 | Bazell et al. ...................... 128/351 |
| 3,903,893 | 9/1975 | Scheer ............................. 128/325 |
| 3,981,299 | 9/1976 | Murray ............................ 128/349 |
| 4,030,504 | 6/1977 | Doyle .............................. 128/325 |
| 4,158,916 | 6/1979 | Adler ................................. 32/33 |
| 4,182,385 | 1/1980 | Williamson ....................... 141/65 |
| 4,233,025 | 11/1980 | Larson et al. .................... 433/136 |
| 4,243,035 | 1/1981 | Barrett ............................. 128/215 |
| 4,315,505 | 2/1982 | Crandall et al. ............. 128/200.26 |
| 4,338,941 | 7/1982 | Payton ............................. 128/325 |
| 4,488,548 | 12/1984 | Agdanowski ................. 128/207.15 |
| 4,508,533 | 4/1985 | Abramson ......................... 604/45 |
| 4,568,326 | 2/1986 | Rangaswamy ...................... 604/1 |
| 4,584,998 | 4/1986 | McGrail ....................... 128/207.15 |
| 4,606,346 | 8/1986 | Berg et al. ....................... 128/342 |

FOREIGN PATENT DOCUMENTS

| | | | |
|---|---|---|---|
| 2341833 | 2/1975 | Fed. Rep. of Germany ...... 128/325 |
| 220978 | 6/1968 | Sweden ............................ 128/342 |

OTHER PUBLICATIONS

Bernhard et al., "Intracuff Pressures in Endotracheal and Tracheostomy Tubes," Chest, /87/6/Jun. 1985, pp. 720–725.

Robischon, Thomas, "Orange County, CA: A Hotbed of Medical-Technology Entrepreneurship," Medical Device & Diagnostic Industry, vol. 10, No. 1, Jan. 1988, pp. 36–39.

Pamphlet: "Shiley's Family of Tracheostomy Products," Shiley Inc., 1987.

*Primary Examiner*—Dalton L. Truluck
*Attorney, Agent, or Firm*—Knobbe, Martens, Olson & Bear

[57] ABSTRACT

A nasal tampon, adapted for use during a nasal surgery comprises an expansible low pressure sealing cuff, an inflation conduit, a drainage conduit, and an absorptive member. The tampon is designed to control nasal hemorrhaging without exerting direct pressure on the bleeding area. The expansible cuff conforms to the inner walls of the choanae and forming a seal therebetween so as to occlude the passageway and thereby prevent the flow of blood and other fluids down the patient's throat.

13 Claims, 2 Drawing Sheets

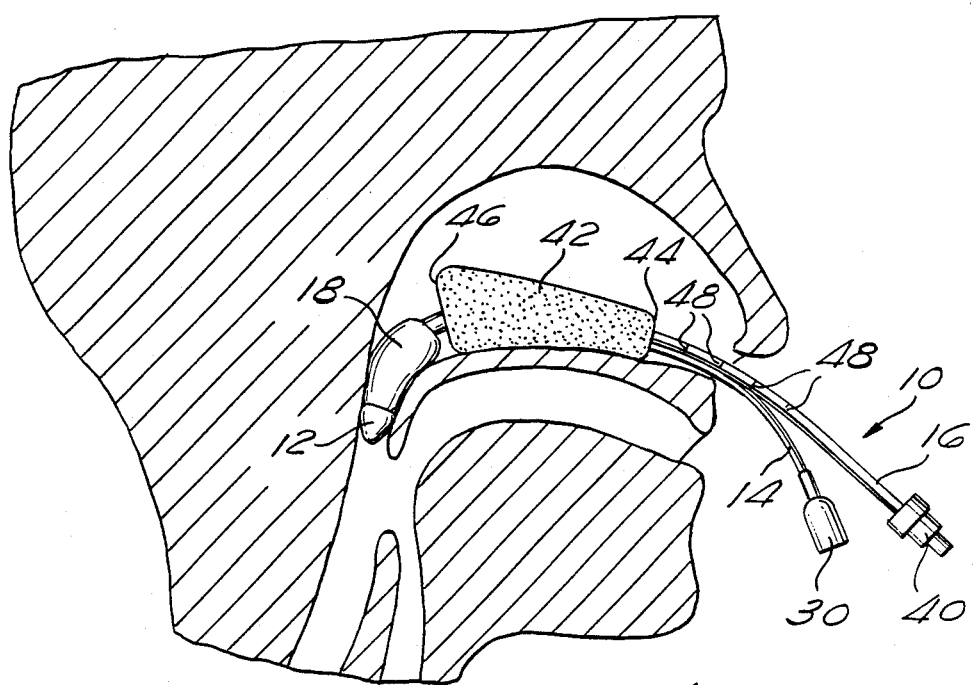
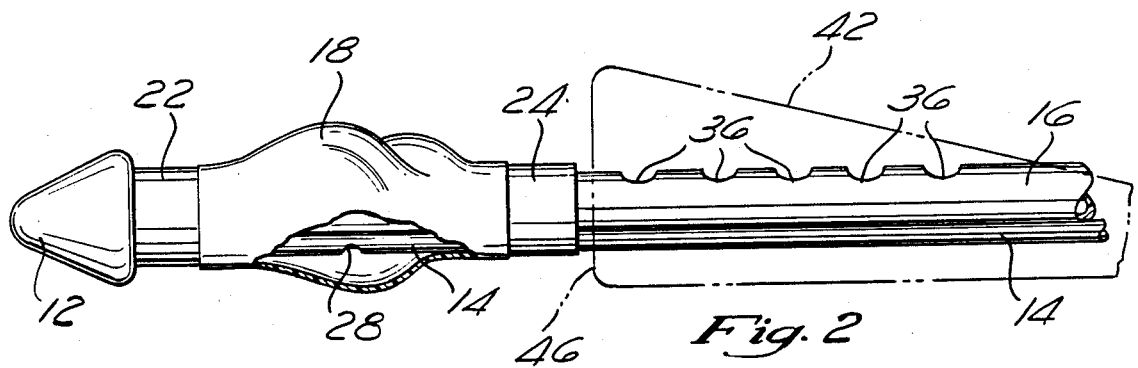
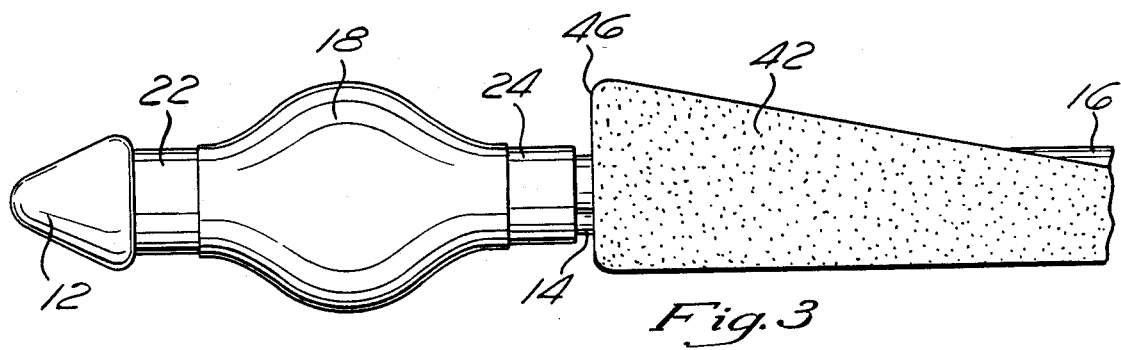

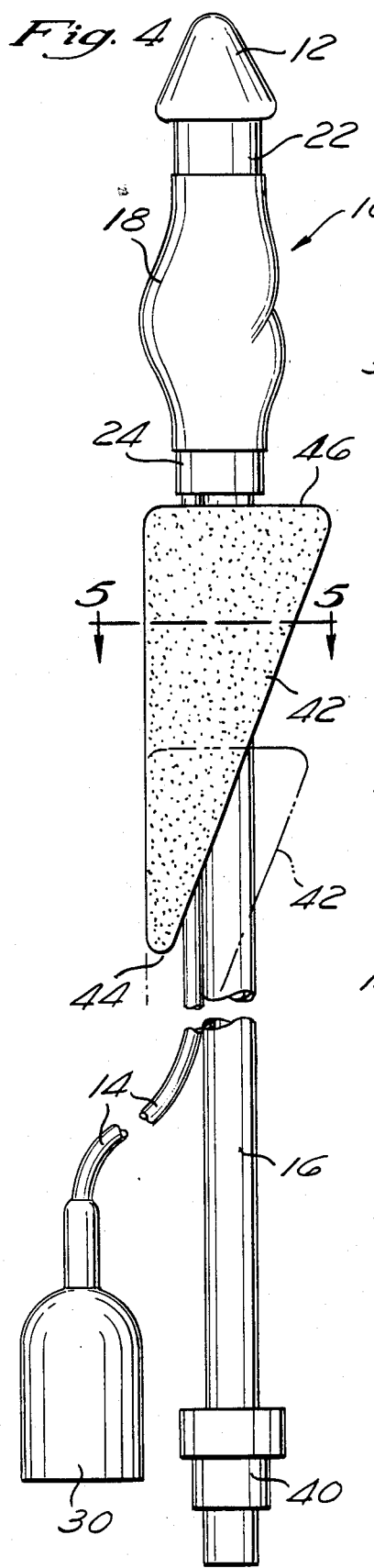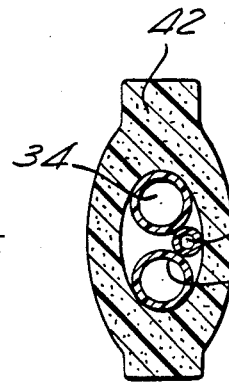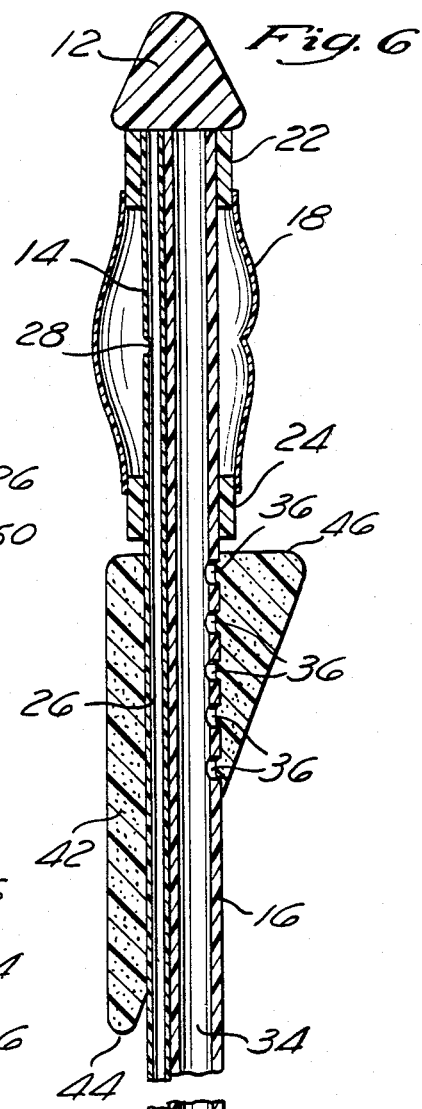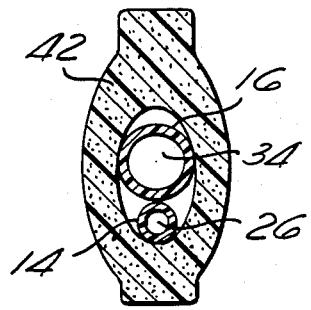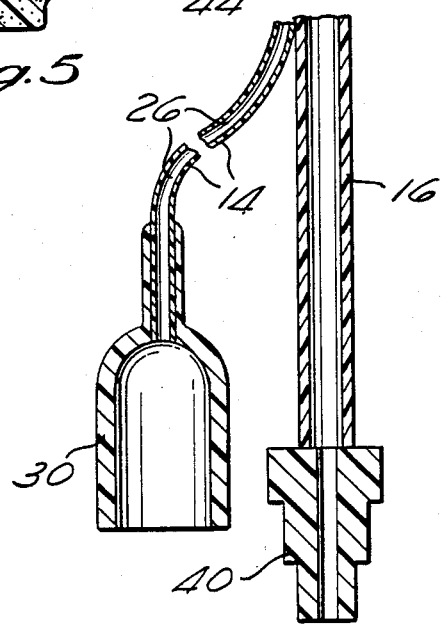

NASAL TAMPON AND METHOD FOR USING

BACKGROUND OF THE INVENTION

This invention relates to nasal tampons and, in particular, to an improved nasal tampon which is designed to occlude the choanae and at the same time permit aspiration of blood and other fluids seeping from an incision or wound. Although the apparatus of the present invention may be adapted to any of a variety of applications, it is particularly useful during and/or following rhinoplasty or other reconstructive or corrective surgical procedures in the vicinity of the nose.

Traditionally, nasal tampons have been used to arrest nasal hemorrhaging by exerting pressure on the area of bleeding. The general practice has been to pack the nasal cavity with absorbent material such as cotton, gauze and the like until a clot is formed and healing commenced. Use of such tampons typically causes a considerable amount of discomfort to the patient and can additionally damage the nasopharyngeal passageway due to pressure necrosis.

In the case of posterior nasal packing, a gauze or sponge plug secured to a catheter may be inserted through the anterior nares into the nasal cavity. The catheter is guided through the posterior choanae into the oral cavity and an end of the catheter is pulled out through the mouth, so as to draw the gauze or sponge plug up against the posterior choanae. As the sponge or gauze-like material fills with blood and other liquids, it swells and begins to occlude the choanae. However, as the sponge continues to absorb the fluids seeping from the incision or wound, the absorptivity decreases, and eventually, fluids escape the sponge and trickle down the patient's throat. When this occurs, the tampon must be removed, and a fresh tampon inserted. Since the sponge or gauze-like material of the tampon has a tendency to adhere to scabs and/or scar tissue within the nasal cavity, removal of the tampon can and often does result in additional bleeding. Further, while the tampon is being replaced, blood and other fluids are allowed to flow freely from the wound or incision and into the trachea.

In an attempt to overcome the problems encountered with these gauze-like types of nasal tampons, catheter-like devices, having inflatable cuffs have been employed in the prior art. These catheters are inserted through the anterior nares in a deflated state, and after being properly positioned within the nasal cavity, the cuff is inflated to exert pressure on the bleeding area, and thereby arrest hemorrhaging. The inflatable cuffs used in the prior art nasal devices typically require use of sufficiently high pressure that may severely injure the tender mucosal membrane by prolonged contact therewith.

Further, if the nasal tampon is to be used during a surgical procedure to control hemorrhaging, it is imperative that sufficient working room is left for the surgeon. Nasal tampons which control bleeding by direct pressure are inappropriate for such surgical procedures, as the area to be operated upon is obstructed by the very nature of these types of tampons.

Aspirating devices are also commonly used to expel blood, mucous and other debris, occasioned by a surgical procedure. Such devices, however, frequently fail to prevent a portion of the fluids from entering the patient's throat. Moreover, direct contact between the intake of an aspirating device and the soft surrounding tissue can cause damage to the nasal mucosa and can contribute greatly to patient discomfort.

SUMMARY OF THE INVENTION

The present invention provides a novel nasal tampon which is readily adaptable to a variety of patient anatomies, and which eliminates many of the problems of prior art nasal tampons.

The present invention also provides a nasal tampon capable of suctioning out blood, mucous and other fluids present in the nasal cavity of a patient, due to a wound or incision without risk of direct suctioning of the soft surrounding tissue.

A significant feature of the preferred embodiment of the present invention is that it provides a nasal tampon having an expansible low pressure sealing cuff, constructed such that, when in the inflated condition, it presents an extended, low pressure cylindrical sealing surface for contacting the inner walls of the nasopharyngeal passageway with only a light pressure, while very effectively occluding the choanae to substantially eliminate the flow of blood and other liquids down the throat of a patient.

Another significant advantage of the invention is that it controls hemorrhaging without direct pressure to the wound and leaves at least the frontal one-third of the nasal cavity clear for the performance of the surgical procedure.

These, as well as other features of the invention will become apparent from the detailed description of preferred embodiments which follows, considered together with the appended drawings.

BRIEF DESCRIPTION OF THE DRAWINGS

FIG. 1 is a diagrammatical elevational view of a human head illustrating a nasal cavity and a preferred embodiment of the improved nasal tampon of the present invention, operatively installed within the nasal cavity;

FIG. 2 is a perspective view of a preferred embodiment of the present invention, showing an absorptive sponge in phantom lines and a partial cut away view of the expansible cuff, in a deflated state;

FIG. 3 is a perspective view of the intranasal portion of the improved nasal tampon of the present invention, showing the expansible cuff in an inflated state;

FIG. 4 is a perspective view of the improved nasal tampon of the present invention, showing, in phantom lines, the ability of the sponge to move laterally along the inflation and drainage conduits;

FIG. 5 is a cross-sectional view, taken along line 5-5 of FIG. 4, showing the sponge and lumen arrangement;

FIG. 6 is a cross-sectional longitudinal view, of the apparatus shown in FIG. 4 and FIG. 7 is a cross-sectional view, similar to FIG. 5, but of an alternative embodiment, showing a third lumen which provides a breathing passageway, which enables the patient to breathe through the nose while the device is operatively installed.

DETAILED DESCRIPTION OF THE PREFERRED EMBODIMENT OF THE NASAL TAMPON

Referring now to the drawings in detail, wherein like reference numerals designate like elements throughout the several views thereof, there is shown generally at 10, a nasal tampon, embodying the present invention in a preferred form, positioned in a nasal cavity in an inflated condition. The tampon 10 is a flexible device of sufficiently small diameter, which enables the tampon, in its deflated state, to be threaded through the anterior nares of a patient in catheter-like fashion. As shown in FIGS. 1, 4 and 6, the tampon 10 is tubular in shape, and comprises a blunt, tapered guiding end, having an inflation conduit 14 and a drainage conduit 16 contiguous therewith.

An expansible low pressure sealing cuff 18 surrounds the distal ends of the inflation and drainage conduits. The cuff 18 is constructed so that in the inflated condition it presents an extended cylindrical sealing surface for contacting the inner walls of the nasopharyngeal passageway. The cuff is sized so that, in its inflated state, it conforms to the interior walls of the choanae to occlude the passageway, yet does not interfere with the patient's swallowing or respiration through the mouth. By utilizing a cylindrically shaped surface, a low pressure seal may be formed with the choanae without applying excessive air pressure, since the seal extends over an extended axial length of the choanae. This extended surface allows an adequate seal to be formed so that only a low intracuff pressure of under 25 mmHg is applied to the soft mucosal tissue and therefore substantially eliminates the risk of damage due to pressure necrosis.

The guiding end 12 of the tampon 10 is preferably rounded and tapered, with no sharp edges to prevent damage to the mucous membrane, nerves and/or blood vessels when the device 10 is installed within the nasal cavity, and also to allow a fairly smooth surface continuation of the expansible low pressure sealing cuff 18. The expansible sealing cuff 18 is closed at opposite ends by a sealing attachment of its open ends to traverse walls 22, 24 respectively.

Extending longitudinally through the expansible low pressure sealing cuff 18 is a continuous, flexible hollow inflation conduit 14. The inflation conduit 14 has a small diameter, axially extending tubular passageway 26, having an opening 28 within the cavity of the expansible low pressure sealing cuff 18. The tubular passageway 26 is adapted to permit air or other pneumatic fluid to be transmitted through the tube and into the chamber enclosed by expansible low pressure sealing cuff 18 for inflation and deflation thereof.

To facilitate inflation of the expansible low pressure sealing cuff 18, a simple fluid valve 30 may be attached at the distal end of the conduit 14. This valve 30 is thus integrally connected to the inflation conduit 14 and may be easily manipulated to allow quick sealing of the pneumatic inflation conduit 14. The expansible low pressure sealing cuff 18 may be pressurized by inserting a hypodermic syringe (not shown) into the end of the inflation conduit 14 or, more preferably, into an enlarged opening (not shown) in the valve 30, with the valve in its open condition. By forcing air into the inflation conduit 14 with the hypodermic syringe, the expansible low pressure sealing cuff 18 may be inflated. It has been determined that approximately only 5 to 10 cc's of air will be sufficient to inflate the cuff 18 to a level which will provide an adequate seal with the choanae and thereby occlude the passageway. The valve 30 may then be closed and the hypodermic syringe removed, leaving the expansible low pressure sealing cuff 18 in an inflated state.

Adjacent to the inflation conduit 14 is a continuous, flexible hollow drainage conduit 16. As shown in FIG. 2, the drainage conduit 16, in relation to the inflation conduit 14, has a somewhat enlarged diameter, axially extending tubular passageway 34, having a plurality of influent ports 36, adjacent to the distal end thereof. Disposed at the proximal end of the drainage conduit 16, and integrally connected thereto, is a coupling device 40. The coupling device 40 provides a means by which the drainage conduit 16 may be connected to a source of suction (not shown), so as to expel blood and other debris, accumulated in front of the sealing cuff 18 from the nose of the patient. Well adapted to this purpose are leur type couplers, commonly used in connection with medical devices, friction fit couplers, or any conventional coupler which can be adapted to be connected to a source of suction.

When using such suction types of devices, it is important that surrounding tissue is not inadvertently aspirated with the rest of the blood and other fluids which are desired to be expelled. Such aspiration of the tissue not only hampers the function of the device, but also causes great discomfort to the patient. To ensure that the soft tissue in the immediate vicinity of the influent ports 36 of the drainage conduit 16 are not suctioned into the device, a porous absorptive member 42 is provided. The absorptive member 42 is slidably mounted around the inflation and drainage conduits 14, 16, respectively, and serves to cover the influent ports 36 of the drainage conduit 16. In addition to preventing tissue from being suctioned into the influent ports 36 of the drainage conduit 16, the absorptive member 42 also acts to evenly distribute the vacuum across its entire surface.

Preferably, the absorptive member 42 is in the form of a surgical sponge. By way of example, a MEROCEL ® type sponge, as commercially available from and manufactured by American Corp., Mystic, Calif. 06355 may be employed. As depicted in the drawings, the absorptive member 42 advantageously has a tapered configuration such that the proximal end 44 has a smaller cross-sectional area than the distal end 46 thereof. This arrangement allows maximum absorptivity, while leaving sufficient working room for the surgeon to perform the surgical procedure. Preferably, the absorptive member 42 is sized so as to maintain at least the frontal one-third of the nasal cavity substantially clear. Further, as shown in FIG. 4, because the absorptive member 42 is slidably mounted around the inflation and drainage conduits, it may be slid laterally along the inflation and drainage conduits so as to provide additional working room, as required.

A material which is well adapted to construction of the present nasal tampon 10 is Poly Vinyl Chloride (PVC), such as Firestone's EXON No. 654 or Borden's VC-2605, made flexible with approximately 50% of a plasticizer, such as dioctyl phthalate. The conduits 14, 16 may be formed by injection molding from compounds such as Maclin's VM 2800 and VM 0400. Any conventional inert plasticizer such as adipate plasticizers or other phthalate esters can be used. The expansible low pressure sealing cuff 18 is formed with a higher quality of plasticizer to provide a greater flexibility.

The inflation conduit 14, drainage conduit 16, and expansible low pressure sealing cuff 18 are preferably constructed out of the same non-toxic polymer material. Dielectric heating of the polyvinyl chloride may be used to bind the ends 22, 24 of the cuff 18 to the inflation and drainage conduits 14, 16, respectively. The heating fuses the surfaces of these members into one another, and thus forms an integral pneumatic sealing bond.

Alternatively, a plastisol may be used as a bonding agent to fix the ends of the sealing cuff 18 to the inflation and drainage conduits. By heat curing the plastisol, an air tight bond may be formed.

Alternative Embodiment of the Nasal Tampon

Due to the nature of the expansible low pressure sealing cuff 18, the nasal tampon 10 of the present invention can be operatively installed for any length of time: from a matter of minutes to a matter of days, without causing necrosis to the tissue with which it comes in contact. When the device is to be left in the nasal cavity for a prolonged period of time, it is preferable that breathing through the nose be permitted.

To this end, in an alternate embodiment, a third conduit 50, as shown in cross-section in FIG. 7, is provided. This breathing conduit 50 extends longitudinally through the expansible low pressure sealing cuff 18 and out the guiding end 12 of the tampon 10, bypassing the seal formed between the cuff 18 and the choanae. Thus, the patient is allowed to breathe through the nasal cavity in which the device is operatively installed.

Manner of Use of the Nasal Tampon

The nasal tampon 10 of the present invention is adapted to control nasal hemorrhaging due to any number of causes. For a simple nasal hemorrhage which, for example, may be nothing more than a common nose bleed, the device 10 may be inserted through the anterior nares of the nasal cavity in its deflated state. Once the device 10 is properly situated within the nasal cavity, the expansible sealing cuff 18 is inflated to a level just sufficient to occlude the choanae, so as to eliminate the flow of blood down the throat of the patient.

To assist in the proper placement of the device 10, a plurality of graduated markings 48 may be provided on one or both the inflation or drainage conduits 14, 16, respectively. The drainage conduit 16 ay then be attached to a source of suction (not shown) so as to void the nasal cavity of all fluids accumulating in front of the expansible sealing cuff 18. The blood and other liquid matter, collected in front of the sealing cuff 18, will be absorbed by the absorptive member 42, and removed therefrom through the influent ports 36 of the drainage conduit 16, and subsequently disposed of.

When the device 10 is to be used during a surgical nasal procedure, the patient is prepared in the standard way. To ensure the continued satisfactory operation of the device 10, it is desirable to line the device with a polymeric organic silicon compound which will prevent adherence of blood or other liquid matter onto the device 10, and thereby maintain all of the passageways clear. Well suited for this purpose is a ZYLOCANE gel, which serves to lubricate the device as well as provide a local anesthetic to desensitize the area. The nasal tampon 10, in its deflated state, is of a sufficiently small diameter, which enables it to be inserted through the anterior nares of the nose, which may be spread apart using a conventional nasal speculum. No forceps are required, since the tampon 10 may be manipulated much like a catheter. Further, the inflation and drainage conduits 14, 16, respectively, are flexible so as to readily bend and follow the normal front to back curvature of the nasal cavity. The expansible low pressure sealing cuff 18 is readily collapsed around the inflation and drainage conduits 14, 16 to facilitate passage through the nares. Once suitably positioned within the nasal cavity, the expansible sealing cuff 18 may be inflated in the manner discussed above.

The device 10 is also suited for use in post operative situations, for example, following reconstructive surgery. Since the choanae is occluded by the expansible sealing cuff 18, the danger of the patient swallowing and/or choking on his own blood is substantially eliminated.

It will be appreciated that certain structural variations may suggest themselves to those skilled in the art. The foregoing detailed description is to be clearly understood as given by way of illustration, the spirit and scope of this invention being limited solely by the appended claims.

What is claimed is:

1. An intranasal device for controlling nasal hemorrhaging without direct pressure, said device adapted for insertion into a nasal cavity during a nasal operation or other nasal procedure for (i) occluding the choanae to prevent blood and other fluids from flowing from the nose into the patient's throat, and (ii) expelling blood, mucous and other debris from the nasal cavity, without direct suctioning of the soft surrounding tissue, said device comprising:
   an elongated tubular element, having mounted thereon a blunt, tapered guiding end, adapted to facilitate manipulation of said device within the nasal cavity;
   an expansible low pressure sealing cuff, contiguous with said guiding end and adapted to be inflated by a source of pressurized fluid;
   an inflation conduit, having a tubular passageway, for transmitting said pressurized fluid into and out of said expansible low pressure sealing cuff, so as to inflate and deflate said cuff, respectively;
   a drainage conduit, adapted to be connected to a source of suction, said drainage conduit exhibiting a plurality of influent ports which enable blood, mucous, and other liquid debris to be suctioned from the nasal cavity; and
   an absorptive member, adapted to enclose said influent ports of said drainage conduit so as to prevent soft tissue present in the nasal cavity from being suctioned into said influent ports and to evenly distribute said suction over substantially the entire surface area of said absorptive member.

2. An apparatus as defined by claim 1, wherein said absorptive member comprises a surgical sponge.

3. An apparatus as defined by claim 2, wherein said surgical sponge has a proximal end and a distal end, said proximal end exhibiting a smaller cross-sectional area than said distal end so as to provide maximum absorptivity, while leaving adequate room for said surgical procedure.

4. An apparatus as defined in by claim 3, wherein said surgical sponge is sized such that at least the frontal one-third of the nasal cavity is left clear for the performance of said nasal procedure.

5. An apparatus as defined by claim 1, wherein said absorptive member is slidably mounted to said inflation and drainage conduits.

6. An apparatus as defined by claim 1, wherein said device is coated with a lubricant to prevent adherence of blood or other liquid matter to the device.

7. An apparatus as defined by claim 6, wherein said lubricant is a Zylocane gel.

8. An apparatus as defined by claim 1, further comprising a breathing conduit, said breathing conduit adapted to bypass said expansible sealing cuff, so as to allow breathing through the nostril in which the device is operatively installed.

9. An intranasal device for controlling nasal hemorrhaging without direct pressure, said device adapted for insertion into a nasal cavity during a nasal operation or other nasal procedure, said device comprising:
    an elongated tubular element, having mounted thereon a blunt, tapered guiding end, adapted to facilitate manipulation of said device within the nasal cavity;
    an expansible low pressure sealing cuff, contiguous with said guiding end and adapted to be inflated by a source of pneumatic fluid;
    an inflation conduit, having a tubular passageway for transmitting said pneumatic fluid into and out of said expansible low pressure cuff, so as to inflate and deflate said cuff, respectively;
    a drainage conduit, adapted to be connected to a source of suction, said drainage conduit exhibiting a plurality of influent ports which enable blood, mucous and other debris to be suctioned from the nasal cavity; and
    an absorptive member, having a tapered configuration, exhibiting a smaller cross-sectional area at its proximal end and a larger cross-sectional area at its distal end, said tapered configuration adapted to provide maximum absorptivity within the nasal cavity, while leaving a substantial portion of the frontal nasal cavity clear for said nasal procedure, said absorptive member adapted to enclose said influent ports of said drainage conduit, so as to prevent soft tissue present in the nasal cavity from being suctioned into said influent ports and to evenly distribute said suction over substantially the entire surface area of said absorptive member.

10. An intranasal device for controlling nasal hemorrhaging within the nasal cavity, without exerting direct pressure on the area of bleeding, said device comprising:
    an elongate tubular body, having a blunt tapered guiding end, said tubular body including an inflation conduit and a drainage conduit;
    an expansible low pressure sealing cuff, contiguous with said guiding end and adapted to be inflated by a source of pressurized fluid such that when inflated, said cuff will form a low pressure seal with the choanae of the patient so as to occlude the passageway, said sealing cuff adapted to readily collapse around said tubular body when deflated, so as to facilitate passage through the anterior nares; and
    an absorptive member, encircling said tubular body adjacent said expansible sealing cuff, said absorptive member adapted to absorb blood, mucous and other fluids present in the hemorrhaging nasal cavity, and to channel said fluids toward said drainage conduit.

11. An apparatus as defined by claim 10, wherein said drainage conduit exhibits a plurality of influent ports which are covered by said absorptive member.

12. An apparatus as defined by claim 11, wherein said drainage conduit is connected to a source of suction, so as to void the nasal cavity of said fluids accumulated in front of said expansible sealing cuff.

13. An apparatus as defined by claim 10, further comprising a breathing conduit, said breathing conduit adapted to bypass said expansible sealing cuff, so as to allow breathing through the nostril in which the device is operatively installed.

* * * * *